United States Patent [19]

Kinzer et al.

[11] 4,122,165

[45] Oct. 24, 1978

[54] INSECTICIDAL COMPOSITION CONTAINING CIS-9-TRICOSENE AND METHOMYL

[75] Inventors: David R. Kinzer, Louisville; Joe D. McDaniel, Dallas, both of Tex.

[73] Assignee: Zoecon Corporation, Palo Alto, Calif.

[21] Appl. No.: 833,402

[22] Filed: Sep. 15, 1977

[51] Int. Cl.$^2$ .................... A01N 17/14; A01N 9/12
[52] U.S. Cl. ........................................ 424/84; 424/300
[58] Field of Search .................................. 424/84, 300

[56] References Cited

U.S. PATENT DOCUMENTS 3,576,834  4/1971  Buchanan ........................ 424/304

FOREIGN PATENT DOCUMENTS 477,526  5/1975  Australia.

*Primary Examiner*—Donald B. Moyer
*Attorney, Agent, or Firm*—Donald W. Erickson

[57] ABSTRACT

Novel insecticidal composition for the control of Diptera such as *Musca domestica* comprising cis-9-tricosene, methomyl, and a carrier substance.

9 Claims, No Drawings

INSECTICIDAL COMPOSITION CONTAINING CIS-9-TRICOSENE AND METHOMYL

This invention is directed to highly effective insecticidal compositions for Diptera, especially *Musca domestica*.

More particularly, this invention relates to a novel composition comprising cis-9-tricosene, methomyl, and a suitable carrier substance, which is unusually effective for combatting Dipteran insects.

Although the art knows that cis-9-tricosene is a sex pheromone of *Musca domestica* and has been used in combination with insecticides (Australian Pat. No. 477,526) for the control of Dipteran insects, the superior effectiveness of the compositions of the present invention over prior art compositions is unexpected and could not have been predicted.

In the practice of the present invention, cis-9-tricosene is mixed with methomyl together with a suitable carrier substance to prepare the novel compositions of the present invention which are then applied in the usual way for control. One suitable method of preparing the compositions of the present invention is to mix methomyl, with or without solvent or diluent, with a suitable carrier substance and then mix the resulting composition with cis-9-tricosene with or without solvent.

The novel insecticidal compositions of the present inventions can include conventional pest control adjuvants, diluents, modifiers or conditioning agents, herein included in the term "suitable carrier substance", to provide compositions in the form of solutions, emulsions, dispersions, powders, dusts, granules, pellets, and the like. Thus, the insecticidal compositions can be liquid or solid. The liquid compositions can contain one or more surface active agents as a conditioning agent to render the composition readily dispersable in water. The term surface active agents includes wetting agents, dispersing agents, emulsifying agents, and the like. The solid formulations of the present invention in the form of powder, dust, pellets or granules can be prepared using such substances as talc, natural clay, pyrophyllite, diatomaceous earth, walnut shells, corn cobs, sugar and the like.

The amount of active ingredient in the compositions of the present invention will vary according to the manner in which the composition is to be applied but, in general, will be from about 0.25% to 95% by weight of the total composition. Usually, the amount of active ingredient will be about 0.50% to 10%. Active ingredient as used herein means cis-9-tricosene and methomyl. The ratio of cis-9-tricosene to methomyl is generally from about 1:50 to 25:1 parts by weight. A sugar granule formulation of 1% methomyl and containing cis-9-tricosene within the ratio of 1:25 to 2:1 of cis-9-tricosene to methomyl provides an increase in effectiveness of a few hundred percent to several hundred percent over the same granule formulation containing other insecticides such as propoxur (o-isopropoxyphenyl methylcarbamate). A comparison of a sugar granule formulation of methomyl and propoxur in the absence of cis-9-tricosene shows substantially equal effectiveness.

Methomyl is the common name for methyl N-thioacetamide, described in U.S. Pat. No. 3,576,834. As described in U.S. Pat. No. 3,576,834, other pesticides can be used in mixture with methomyl. The mixtures taught and described in U.S. Pat. No. 3,576,834 are hereby incorporated herein by reference. It is important, however, that within the practice of the present invention the ratio of cis-9-tricosene to methomyl remain within the ratios described herein even though other pesticide(s) may be present in the composition.

The following examples are provided to illustrate the practice of the present invention and not as a limitation of the scope thereof. All parts and percentages are by weight.

EXAMPLE 1

The formulations below were prepared by dissolving the active ingredient, methomyl or propoxur, in methylene chloride and blending with fine grain beet sugar of relatively uniform particle size until homogenous. The formulations containing cis-9-tricosene were prepared by dissolving the cis-9-tricosene in methylene chloride and then thoroughly blending with the formulation of sugar and active ingredient until dry and flowable.

| Formulation | | Parts |
|---|---|---|
| A) | propoxur | 1 |
| | sugar | 10 |
| B) | methomyl | 1 |
| | sugar | 10 |
| C) | propoxur | 1 |
| | sugar | 10 |
| | cis-9-tricosene | 0.1 |
| D) | methomyl | 1 |
| | sugar | 10 |
| | cis-9-tricosene | 0.1 |

Formulations A, B, C and D were tested in a large swine house, using the formulations as a scatter bait. The results are tabulated in Table 1. The superior effectiveness of formulation D, a composition of the present invention, is evident. Trials were ended after 30 minutes. The number of dead flies were counted at 15 minutes and 30 minutes. For convenience, the mean fly count is given as a ratio. In each test, 0.8 grams per four square feet of each formulation was used.

Table 1

| Formulation | Mean Fly Count (ratio) |
|---|---|
| A | 1.0 |
| B | 1.0 |
| C | 2.2 |
| D | 4.6 |

Trials were made using formulations A-D at a large poultry house. The formulations were scattered using 0.8 grams per four square feet. Counts were made after 15 and 25 minutes and the trial terminated.

Table 2

| Formulation | Mean Fly Count (ratio) |
|---|---|
| A | 2.0 |
| B | 1.0 |
| C | 6.0 |
| D | 14.4 |

At a second site of the large poultry house, formulations C and D were tested using 0.8 grams per four square feet ground area. Two replicates of each test were made and counts were made after 30 minutes.

Table 3

| Formulation | Mean Fly Count (ratio) |
|---|---|
| C | 1.0 |

Table 3-continued

| Formulation | Mean Fly Count (ratio) |
|---|---|
| D | 7.3 |

EXAMPLE 2

Formulation E was prepared using the procedure of Example 1 and containing 1% methomyl and 0.04% cis-9-tricosene with fine granule sugar as the carrier. Formulations B, D and E were tested using equal quantities of each in a scatter test at an egg ranch. The tests were terminated after 4 hours.

Table 4

| Formulation | Mean Fly Count (ratio) |
|---|---|
| B | 1.0 |
| D | 7.5 |
| E | 4.6 |

Formulations utilizing diatomaceous earth of about 8 mesh or less particle size, methomyl and cis-9-tricosene are prepared as in Examples 1 and 2. The formulations are useful for *Musca domestica* control around stockyards, patios, chicken houses, etc., by scattering.

WHAT IS CLAIMED IS:

1. An insecticidal composition comprising a mixture of cis-9-tricosene, methomyl and a suitable carrier substance.
2. A composition according to claim 1 wherein said carrier substance is sugar.
3. A composition according to claim 2 wherein said mixture contains cis-9-tricosene and methomyl in the total amount of from 0.25% to 95%, by weight, of the composition.
4. A composition according to claim 3 wherein the ratio of cis-9-tricosene and methomyl is from about 1:50 to 25:1.
5. A composition according to claim 4 wherein said ratio is from about 1:25 to 2:1.
6. A composition according to claim 5 wherein the total amount of cis-9-tricosene and methomyl is from about 0.50% to 10%.
7. A composition according to claim 6 wherein the sugar is granulated sugar.
8. A method of destroying Diptera insects which comprises applying to the locus to be protected a mixture containing cis-9-tricosene, methomyl and a suitable carrier substance.
9. The method according to claim 8 wherein the carrier substance is granulated sugar.

* * * * *